Figure 1:
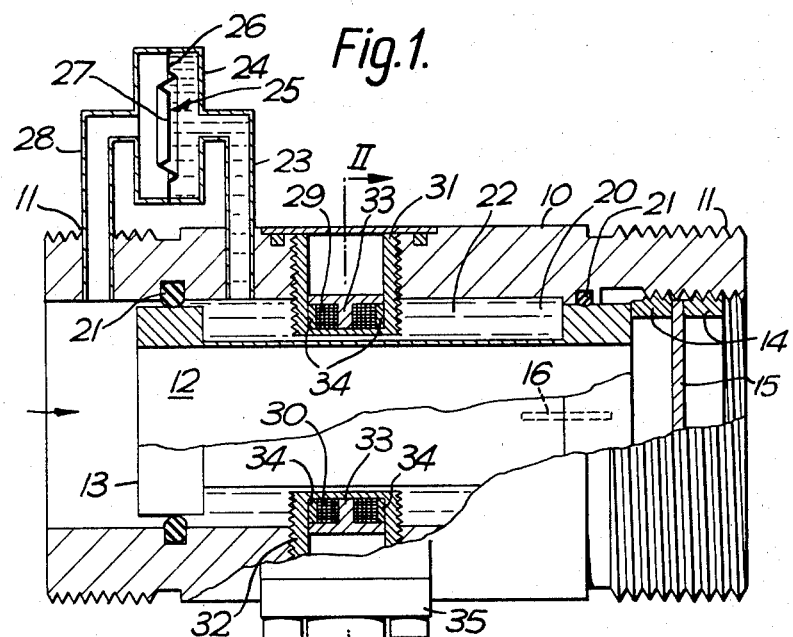

United States Patent [19]

Agar

[11] 3,983,744
[45] Oct. 5, 1976

[54] METHOD AND APPARATUS FOR MEASURING THE DENSITY OF A DIRTY FLUID

[75] Inventor: Joram Agar, Houston, Tex.

[73] Assignee: Agar Instrumentation, Inc., Houston, Tex.

[22] Filed: Aug. 4, 1975

[21] Appl. No.: 601,478

[30] Foreign Application Priority Data
Aug. 8, 1974 United Kingdom............... 35009/74

[52] U.S. Cl................................................ 73/32 A
[51] Int. Cl.² .......................................... G01N 9/00
[58] Field of Search........................... 73/32 R, 32 A

[56] References Cited
UNITED STATES PATENTS
3,648,512   3/1972   Abbotts .............................. 73/32 A
3,763,692   10/1973   Agar ................................... 73/32 A Primary Examiner—James J. Gill
Attorney, Agent, or Firm—John W. Logan, Jr.

[57] ABSTRACT

Apparatus for measuring the density of a dirty fluid, said apparatus comprising a hollow body adapted to have said dirty fluid passing through its interior; a rigid support member within which the hollow body is mounted and to which it is connected to provide a space therebetween adapted to contain a clean fluid; drive means for exciting said hollow body to vibrate at a resonant frequency; detecting means for detecting a density signal representative of the frequency of such vibrations, the frequency of said density signal in operation being dependent upon the density of said dirty fluid; and pressure transmitting means for transmitting the pressure of dirty fluid passing through the interior of the hollow body to the clean fluid in said space, so that the exterior of the hollow body is always subjected to substantially the same pressure as the interior thereof.

12 Claims, 7 Drawing Figures

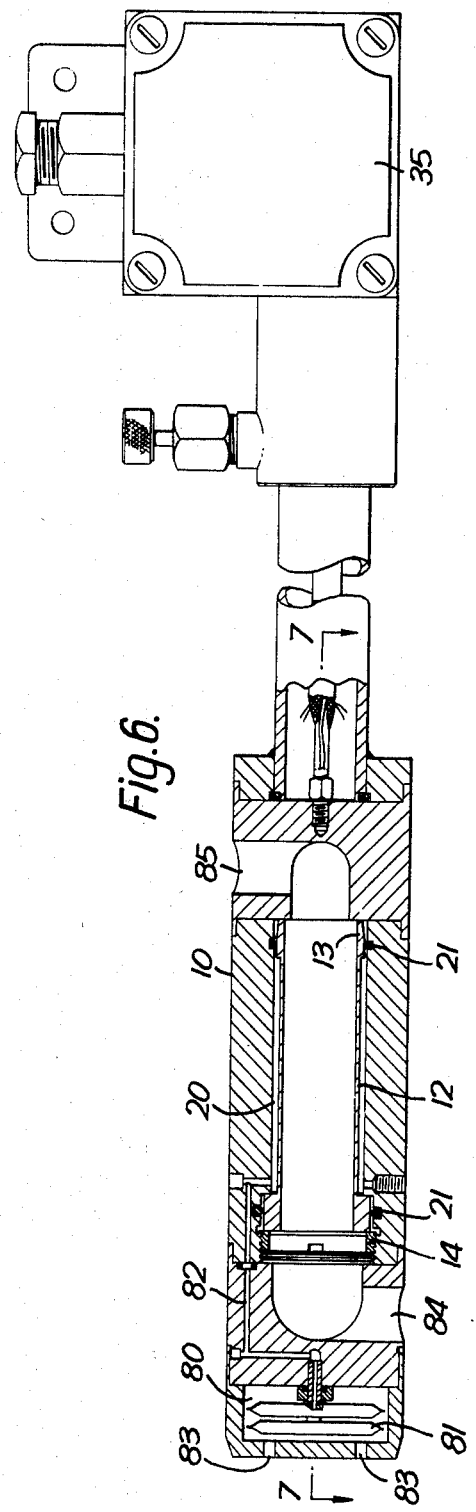
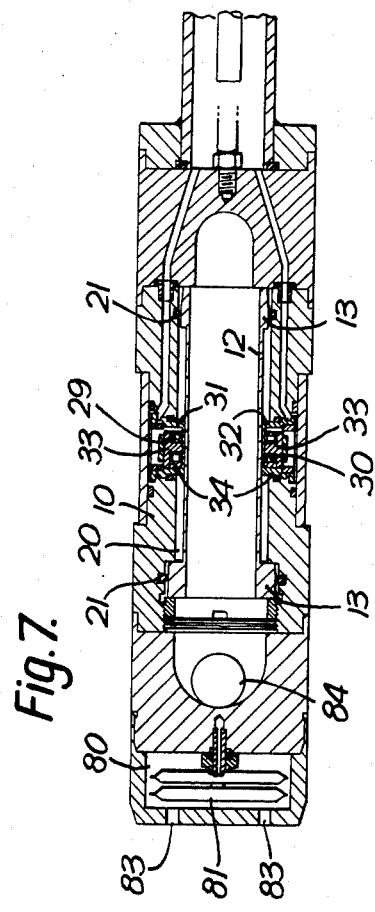
Fig.6.
Fig.7.

METHOD AND APPARATUS FOR MEASURING THE DENSITY OF A DIRTY FLUID

This invention concerns a method and apparatus of measuring the density of a dirty fluid.

In British Patent Specification No. 1,175,586, there is disclosed a method and apparatus for measuring the density of a fluid in which the fluid is passed through the interior of a hollow body which is itself mounted within and spaced by a gap from a rigid support member, so that a portion of the fluid flows through the said gap so as to equalise the fluid pressures acting on the hollow body. Such equalisation of the fluid pressure is desirable since otherwise the density indication provided will depend, inter alia, upon the pressure of the fluid whose density is being measured.

If, however, the fluid whose density is being measured is dirty, then (unless the apparatus is periodically cleaned) dirt may build up in the said gap, and if a sufficient amount of dirt were allowed to accumulate there might, in the end, be little or no flow through the said gap. If that were to occur, then the extent to which there would be equalisation of the pressures acting on the hollow body would be reduced, with a consequent reduction in the accuracy of the density indication provided. In fact, if sufficient dirt were to become trapped in the said gap, the frequency of vibration of the hollow body itself could be affected, with consequent substantial reduction in the accuracy of measurement. Thus if the apparatus of British Patent No. 1,175,586 is used for measuring the density of a dirty fluid, frequent cleaning of the apparatus is necessary.

According to the present invention, there is provided apparatus for measuring the density of a dirty fluid, said apparatus comprising a hollow body adapted to have said dirty fluid passing through its interior; a rigid support member within which the hollow body is mounted and to which it is connected so as to provide a space therebetween adapted to contain a clean fluid; drive means for exciting said hollow body to vibrate at a resonant frequency; detecting means for detecting a density signal representative of the frequency of such vibrations, the frequency of said density signal in operation being dependent upon the density of said dirty fluid, and pressure transmitting means for transmitting the pressure of dirty fluid passing through the interior of the hollow body to the clean fluid in said space, so that the exterior of the hollow body is always subjected to substantially the same pressure as the interior thereof.

Preferably the drive means and the detecting means are carried by said rigid support member adjacent to but externally of and out of contact with the hollow body so that the dirty fluid passes out of contact with said drive means and said detecting means.

Preferably, there are monitoring means for monitoring said density signal.

The clean fluid is also preferably out of contact with said drive means and said detecting means.

The said sealed space preferably contains a clean liquid.

There are preferably compensation means for compensating for the bulk modulus and/or temperature coefficient of the clean liquid so that said density signal is respectively substantially unaffected by the pressure and/or temperature of the dirty fluid.

The pressure transmitting means may comprise a pressure-responsive member opposite faces of which are respectively open to the pressures prevailing in the interior of the hollow body and in said sealed space, the said pressure-responsive member being urged towards a datum position by a force adapted to compensate for the bulk modulus of the clean liquid. Thus the pressure-responsive member may be a spring bellows or diaphragm whose spring rate compensates, or is adjustable to compensate, for the bulk modulus of the clean liquid.

Alternatively, the pressure-responsive member may be engaged by a spring whose spring rate compensates, or is adjustable to compensate, for the bulk modulus of the clean liquid.

The means for compensating for the temperature coefficient of the clean liquid may comprise means for producing a temperature signal representative of the temperature of the clean liquid, and means for employing said temperature signal to modify the density signal so that the value of the latter is substantially unaffected by the temperature of the clean liquid.

Alternatively, the pressure-responsive member may be beengaged by a bi-metallic member with a force such that the said density signal is substantially unaffected by the temperature of the clean liquid.

According to another aspect of the present invention, there is provided a method of measuring the density of a dirty fluid comprising passing the dirty fluid through the interior of a hollow body, the hollow body being mounted within a rigid support member to which it is connected so as to provide a space which contains a clean fluid; transmitting the pressure of the dirty fluid passing through the interior of the hollow body to the clean fluid in the said space, so that the exterior of the hollow body is always subjected to substantially the same pressure as the interior thereof; employing drive means to excite said hollow body to vibrate at a resonant frequency; and employing detecting means to detect a density signal representative of the frequency of such vibrations, the frequency of said density signal being dependent upon the density of said dirty fluid.

Figure 2:
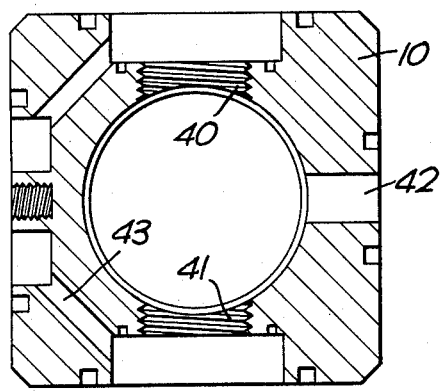
Figure 4:
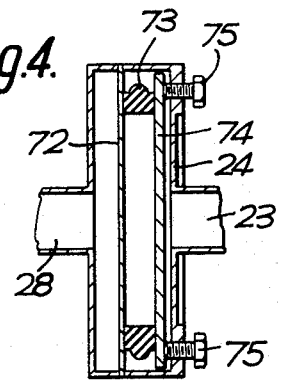
Figure 5:
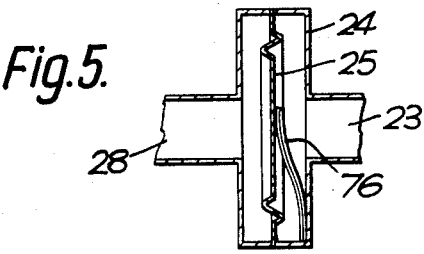
Figure 3:
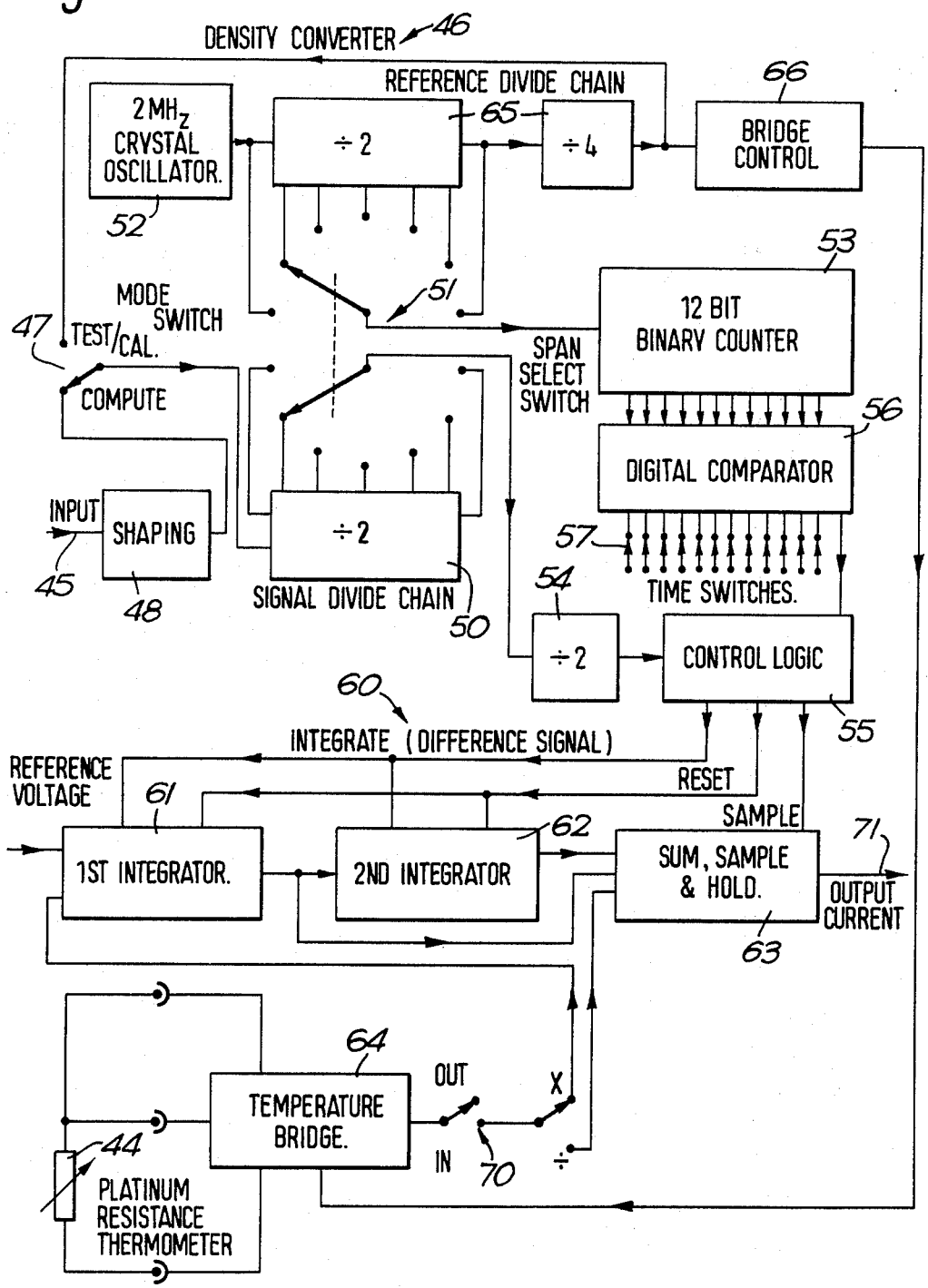

The invention is illustrated, merely by way of example, in the accompanying drawings, in which:

FIG. 1 is a side view, partly in section of a first embodiment of an apparatus for measuring the density of a dirty fluid in accordance with the present invention, FIG. 2 is a cross-sectional view of a rigid support member which forms part of the apparatus of FIG. 1, FIG. 2 being taken on the line 2—2 of FIG. 1, FIG. 3 is a circuit diagram of a density converter which may be used in association with the apparatus of FIG. 1, FIGS. 4 and 5 illustrated modifications of a part of the apparatus of FIG. 1, FIG. 6 is a side view, partly in section, of a second embodiment of an apparatus according to the present invention, and FIG. 7 is a broken-away sectional view taken on the line 7—7 of FIG. 6.

The terms "left" and "right" used in the description below are to be understood to refer to directions as seen in the drawings.

Referring first to FIGS. 1 and 2, an apparatus for measuring the density of a dirty fluid comprises a rigid, hollow, casing 10 which is substantially rectangular in cross-section and which has threads 11 at both its ends for fitting to a pipe-line (not shown) or other location where the density of a dirty fluid is to be measured. The casing 10 completely surrounds a substantially cylindrical thin-walled body 12 mounted within the interior of the rigid casing 10, the said hollow body 12 being also hollow and of circular internal cross-section. Each end of the body 12 is formed with a flange 13 so as to give the body 12 a substantially dumb-bell shape. Whereas, the rigid casing 10 is made of a non-magnetic material such as aluminium or stainless steel, the body 12, hereinafter referred to as a sensing element 12, is made of a magnetic material which has a small thermo-elastic coefficient.

The sensing element 12 is mounted within the rigid casing 10 by means of a pair of lock-rings 14 between which is mounted a filter element 15. The sensing element 12 is therefore readily detachable from the rigid casing 10.

In order to ensure that the sensing element 12 and the rigid casing 10 are accurately positioned with respect to each other, a lock pin 16, which is secured to the rigid casing 10, is provided to interconnect the sensing element 12 and the rigid casing 10. The pin 16 engages in an appropriate aperture (not shown) formed in the sensing element 12. In this way it is ensured that any removal of the sensing element 12, e.g. for cleaning purposes, and its subsequent replacement within the rigid casing 10, will not necessitate adjustment of the remainder of the apparatus described below.

The sensing element 12 is spaced from the rigid casing 10 by a sealed space 20, the sensing element 12 being sealed to the rigid casing 10 by means of "O" ring seals 21. The sealed space 20 contains a clean liquid 22.

The sealed space 20 communicates by way of a pipe 23 with the right hand portion of chamber 24, the pipe 23 passing through the rigid casing 10. The chamber 24 is divided into right and left hand portions by a spring bellows 25 one face 26 of which is open to the pressure of the clean liquid 22, and the opposite face 27 of which is open to the pressure of the dirty fluid which is passing through the sensing element 12. The left hand portion of the chamber 24 commmunicates with the interior of the rigid casing 10, immediately upstream of the sensing element 12, by way of a pipe 28.

Thus the pressure of the dirty fluid passing through the interior of the sensing element 12 will be transmitted, via the spring bellows 25, to the clean fluid 22 in the sealed space 20, so that the exterior of the sensing element 12 is always subjected to substantially the same pressure as the interior thereof.

Mounted at approximately the mid-portion of the rigid casing 10 are two coils 29, 30 which are located to be adjacent the area of maximum vibration amplitude of the sensing element 12. The coils 29, 30 are offset from each other by 180°.

The coils 29, 30 are respectively mounted in cup-shaped containers 31, 32 which are received within and sealed within apertures 40, 41 (FIG. 2) in the rigid casing 10, the cup-shaped containers 31, 32 extending to adjacent the sensing element 12. Thus this construction ensures that the coils 29, 30 are out of contact both with the dirty fluid passing through the interior of the sensing element 12, and also out of contact with the clean liquid 22 in the sealed space 20. The bottom of each of the cup-shaped containers 31, 32 is very thin so as to ensure that the coils 29, 30 are at an optimum spacing from the sensing element 12.

The windings of each of the coils 29, 30 is in a plane substantially at right angles to the plane of FIG. 1. Each coil is housed in a cup-shaped core comprising a central pole piece 33 and an annular magnet 34. This ensures that the flux path length is short, i.e. from the centre pol 33 via the sensing element 12 to the two outer poles 34, and also ensures that, when these coils are connected in an appropriate electrical circuit, the flux paths therefrom do not overlap each other and extend into the sensing element 12 over only a very small portion thereof compared to the total circumference of the sensing element 12. This arrangement reduces or eliminates cross-coupling between the coils 29, 30.

The coil 29 is a drive coil and the coil 30 is a detector or pick-up coil, and these coils are arranged and maintained in operation at a 90° phase-difference as a result of which viscosity effects are substantially reduced or eliminated.

Mounted on the exterior of the rigid casing 10 is an amplifier 35 to which are electrically connected both the drive coil 29 and the detector coil 30. The amplifier 35 itself is connected to a small D.C. power source, e.g. a 12 volt battery, by way of a lead 36, while the output of the amplifier 35 is connected by way of a lead 37 to a density converter 46 which is shown in FIG. 3 and which monitors the density signal.

The rigid casing 10 is provided, at right angles to the apertures 40, 41, with an aperture 42 through which the clean liquid 22 may be introduced into the sealed space 20, means (not shown) being provided for sealing the aperture 42. The rigid casing 10 is also provided with an inclined aperture 43 in which may be mounted a platinum resistance thermometer 44 (see FIG. 3) so as to extend into, and be responsive to the temperature of, the clean liquid 22 in the sealed space 20.

In operation, natural resonant vibrations will be set up and maintained in the sensing element 12 by virtue of the positive feed-back from the detector or pick-up coil 30 to the drive coil 29. The vibrations are initiated by mechanical noise transmitted to the sensing element 12, or by electrical noise occurring in the drive coil 29 when the amplifier 35 is switched into action. These vibrations are in the circumferential mode of vibrations, since the sensing element 12 acts like two bells which are joined together and clamped at the nodal points, namely the flanges 13. Since the pressures internally and externally of the sensing element 12 will be substantially the same, the signal produced at the lead 37 will be substantially independent of the pressure of the dirty fluid passing through the interior of the sensing element 12.

As will be appreciated, ideally, the clean liquid 22 would be incompressible and would have zero temperature coefficient with respect to density, and thus if the bellows 25 (or other pressure equalising member such as a diaphragm or a low friction piston assembly) were perfectly efficient, the instrument would show no pressure coefficient and no temperature coefficient other than that of the sensing element 12.

In practice, however, the clean liquid 22 has a finite bulk modulus with the result that if the clean liquid 22 is at a lower pressure than the dirty fluid, the indicated density is, if not compensated for, lower than should be the case. However, by appropriate selection of the spring constant of the bellows 25 or the diaphragm, a degree of compensation can be achieved to generate the correct pressure differential to compensate for the bulk modulus of the clean liquid 22.

The clean liquid 22, moreover, inevitably has a temperature coefficient with respect to density, and this effectively changes the constants of the apparatus. This effect however, as indicated below, may be compensated by measuring the temperature of either the clean liquid or dirty fluid, and applying analogue or digital correction to the density frequency signal after suitable electronic processing.

As the density of the clean liquid 22 increases, the instrument becomes less sensitive to changes of density in the dirty fluid. Ideally, therefore, the clean liquid 22 should have a low density, a low temperature coefficient, and a high bulk modulus.

If iso-octane is used as the clean liquid, then the low density requirement is satisfied, and provided a very flexible pressure equalising member is used, then it is possible to achieve a pressure coefficient of approximately 1g/l/100 psi, and a temperature coefficient of approximately 1.2 g/l/°C. The sensitivity in this case is approximately 50% of what it would be if, as in the construction of British Patent No. 1,175,586, the dirty fluid were applied to opposite sides of the sensing element 12. This loss of sensitivity, however, is acceptable in many applications, where dirt is the major problem.

If, instead of employing iso-octane as the clean liquid, an aqueous liquid is employed containing 10% by weight glycol, then a pressure coefficient of approximately 0.3g/l/100 p.s.i., is achieved, although the sensitivity in this case is 16% less than in the case of the use of iso-octane.

In the apparatus illustrated in FIG. 1, dirt will build up at each of the opposite ends of the sensing element 12, but this will not impair the performance of the latter since these ends constitute nodes.

Referring now to FIG. 3, the output signal from the lead 37 constitutes an input 45 to the density converter 46 shown therein. The input signal 45 is fed via shaping means 48 and a mode switch 47 to a binary signal divide chain 50. A span select switch 51 is provided so that the output of the signal divide chain 50 is selected in accordance with the required operating density span for the density converter 46.

A highly stable periodic time reference signal is derived from a quartz crystal oscillator 52, this reference signal also being modified by the setting of the span select switch 51. The reference signal from the quartz crystal oscillator 52 is further modified by a 12 bit binary counter 53, the reference period signal being selected as a zero reference point for the density converter 46.

The density signal from the signal divide chain 50 passes by way of a divide chain 54 to control logic 55. The control logic 55 receives the reference signal from the quartz crystal oscillator 52 after passage of the latter through a digital comparator 56. The reference period output signal is thus compared with the modified density signal by a switch timer 57 in the control logic 55 such that the output of the switch timer 57 is the periodic time difference between the input signal 45 and the reference signal from the quartz crystal oscillator 52.

The output signal from the control logic 55 is fed to a frequency to voltage converter 60 incorporating first and second integrators 61, 62. A sum, sample, and hold amplifier 63 receives signals direct from the first integrator 61 and signals which have passed through the second integrator 62, so that a linearising circuit is provided which compensates for the non-linear relationship between the period time of the density signal and measured density.

A temperature bridge 64 receives a signal from the quartz signal oscillator 52 which has passed through a reference divide chain 65 and a bridge control 66. Connected across the temperature bridge 64 is the platinum resistance thermometer 44. Thus a temperature compensating circuit is provided to allow the density signal to be referred to a particular temperature for specific gravity computation. The resulting voltage signal is fed through a fine span adjustment 70 to the sum, sample, and hold amplifier 63. The sum sample and hold amplifier 63 has an output 71 which is an analogue current linearly related to the operating density of the fluid passing through the density meter of FIG. 1.

The platinum resistance thermometer 44 and temperature bridge 64 are thus arranged to provide for compensation for the temperature coefficient of the clean liquid 22, so that the output signal 71 is substantially unaffected by the temperature of the dirty fluid.

The spring bellows 25 is selected to that its srping rate compensates, or is adjustable (by means not shown) to compensate, for the bulk modulus of the clean liquid 22. Consequently the output signal 71 is substantially unaffected by the pressure of the dirty fluid. That is to say, the spring bellows 25 is inherently urged towards a datum position by a spring force adapted to compensate for the bulk modulus of the clean liquid, i.e. the extent to which the latter is compressible. Thus the bulk modulus is compensated for by ensuring that the pressure of the clean liquid 22 is always appropriately less than that of the dirty fluid.

As indicated above this pressure differential can be provided by appropriate design of the spring bellows 25. An alternative arrangement is, however, illustrated in FIG. 4 in which the spring bellows 25 is replaced by a diaphragm 72 which is engaged by one end of a hollow annular rubber spring 73. The opposite axial end of the rubber spring 73 is engaged by a plate 74 whose position within the right hand portion of chamber 24 can be adjusted by means of set screws 75.

The hollow rubber spring 73 has a variable spring rate which varies in accordance with the load imparted thereto. Accordingly, by appropriate adjustment of the position of the plate 74 within the chamber 24, the load on the spring 73 may be varied so as to provide for the required compensation for the bulk modulus of the clean liquid 22.

In the density converter 46 illustrated in FIG. 3, the temperature signal produced by the platinum resistance thermometer 44 is employed to modify the density signal so that the value of the latter is substantially unaffected by the temperature of the clean liquid 22. However, an alternative way of achieving the same result is illustrated schematically in FIG. 5 where the spring bellows 25 is shown as being engaged by a bimetallic member 76 with a force such that the density signal is substantially unaffected by the temperature of the clean liquid 22 and hence by the temperature of the dirty fluid.

In FIGS. 6 and 7 there is shown a second embodiment of an apparatus according to the present invention for measuring the density of a dirty fluid. The embodiment of FIGS. 6 and 7, however, is generally similar to that of FIGS. 1 and 2 and for this reason will not be described in detail, like reference numerals indicating like parts.

In the construction of FIGS. 6 and 7, however, the chamber 24 of FIG. 1, which is disposed radially outwardly of the rigid casing 10, is replaced by a chamber 80 which is disposed axially of the rigid casing 10 and which thus allows the apparatus to be introduced as a probe into a large pipe line through which the dirty fluid flows.

The chamber 80 contains a bellows 81, e.g. of the metal sold under the trade name Inconel X, the interior of which communicates by way of ducting 82 with the space 20 which contains the clean liquid, such clean liquid being, for example, a silicone liquid. The exterior of the bellows 81 is exposed to the pressure of the dirty fluid which enters the chamber 80 by way of apertures 83 in the wall of the latter. The bellows 81 is designed to have a spring rate such as to compensate for the bulk modulus of the clean liquid.

The dirty fluid enters the rigid casing 10 by way of an inlet passage 84 and leaves by way of an outlet passage 85, the passages 84, 85 being ar right angles to the axis of the sensing element 12.

In FIG. 7 the cup-shaped containers 31, 32 are shown as contacting the sensing element 12, but in fact there is a small space therebetween which is too small to be shown in the drawing.

I claim:

1. Apparatus for measuring the density of a dirty fluid, said apparatus comprising a hollow body adapted to have said dirty fluid passing through its interior; a rigid support member within which the hollow body is mounted and to which it is connected to provide a space therebetween adapted to contain a clean fluid; drive means for exciting said hollow body to vibrate at a resonant frequency; detecting means for detecting a density signal representative of the frequency of such vibrations, the frequency of said density signal in operation being dependent upon the density of said dirty fluid; and pressure transmitting means for transmitting the pressure of dirty fluid passing through the interior of the hollow body to the clean fluid in said space, so that the exterior of the hollow body is always subjected to substantially the same pressure as the interior thereof.

2. Apparatus as claimed in claim 1 in which the drive means and the detecting means are carried by said rigid support member adjacent to but externally of and out of contact with the hollow body so that the dirty fluid passes out of contact with said drive means and said detecting means.

3. Apparatus as claimed in claim 1 in which there are monitoring means for monitoring said density signal.

4. Apparatus as claimed in claim 2 in which the clean fluid is also out of contact with said drive means and said detecting means.

5. Apparatus as claimed in claim 1 in which said space contains a clean liquid.

6. Apparatus as claimed in claim 5 comprising compensation means for compensating for the bulk modulus and temperature coefficient of the clean liquid so that said density signal is respectively substantially unaffected by the pressure and temperature of the dirty fluid.

7. Apparatus as claimed in claim 6 in which the pressure transmitting means comprises a pressure-responsive member opposite faces of which are respectively open to the pressures prevailing in the interior of the hollow body and in said space, the said pressure-responsive member being urged towards a datum position by a force adapted to compensate for the bulk modulus of the clean liquid.

8. Apparatus as claimed in claim 7 in which the pressure-responsive member is a member whose spring rate compensates for the bulk modulus of the clean liquid.

9. Apparatus as claimed in claim 7 in which the pressure-responsive member is engaged by a spring whose spring rate compensates for the bulk modulus of the clean liquid.

10. Apparatus as claimed in claim 6 in which the means for compensating for the temperature coefficient of the clean liquid comprises means for producing a temperature signal representative of the temperature of the clean liquid, and means for employing said temperature signal to modify the density signal so that the value of the latter is substantially unaffected by the temperature of the clean liquid.

11. Apparatus as claimed in claim 6 in which the pressure-responsive member is engaged in a bi-metallic member with a force such that the said density signal is substantially unaffected by the temperature of the clean liquid.

12. A method of measuring the density of a dirty fluid comprising passing the dirty fluid through the interior of a hollow body, the hollow body being mounted within a rigid support member to which it is connected so as to provide a space which contains a clean fluid; transmitting the pressure of the dirty fluid passing through the interior of the hollow body to the clean fluid in the said space, so that the exterior of the hollow body is always subjected to substantially the same pressure as the interior thereof; employing drive means to excite said hollow body to vibrate at a resonant frequency; and employing detecting means to detect a density signal representative of the frequency of such vibrations, the frequency of said density signal being dependent upon the density of said dirty fluid.

* * * * *